(12) United States Patent
Bay et al.

(10) Patent No.: US 8,409,656 B2
(45) Date of Patent: Apr. 2, 2013

(54) METHOD OF MANUFACTURING COATED NEEDLE ELECTRODES

(75) Inventors: Lasse Bay, Copenhagen (DK); Marc Skov Hansen, Roskilde (DK); Brian Nielsen, Næstved (DK)

(73) Assignee: AMBU A/S, Ballerup (DK)

( * ) Notice: Subject to any disclaimer, the term of this patent is extended or adjusted under 35 U.S.C. 154(b) by 657 days.

(21) Appl. No.: 12/597,464

(22) PCT Filed: Apr. 25, 2008

(86) PCT No.: PCT/EP2008/055085
§ 371 (c)(1),
(2), (4) Date: Apr. 15, 2010

(87) PCT Pub. No.: WO2008/132172
PCT Pub. Date: Nov. 6, 2008

(65) Prior Publication Data
US 2010/0203232 A1    Aug. 12, 2010

Related U.S. Application Data

(60) Provisional application No. 60/924,054, filed on Apr. 27, 2007.

(30) Foreign Application Priority Data

Apr. 27, 2007  (DK) ................................ 2007 00632

(51) Int. Cl.
*B05D 5/12*   (2006.01)
(52) U.S. Cl. ........................................ 427/58; 427/99.5

(58) Field of Classification Search ............... 427/163.2, 427/434.6, 127, 289, 498, 512, 594, 601, 427/96.9, 99.5, 209; 118/400, 407, 420, 118/423, 428, 500
See application file for complete search history.

(56) References Cited

U.S. PATENT DOCUMENTS 3,204,634 A  9/1965  Koehn
3,575,832 A  4/1971  Johnson

FOREIGN PATENT DOCUMENTS

JP    402259000    * 10/1990
WO   WO 96/22742    8/1996

OTHER PUBLICATIONS

International Search Report from European Patent Office, for International Application No. PCT/EP2008/055085, mailed Oct. 15, 2008.

* cited by examiner

*Primary Examiner* — Michael Cleveland
*Assistant Examiner* — Tabassom Tadayyon Eslami
(74) *Attorney, Agent, or Firm* — Finnegan Henderson Farabow Garrett & Dunner LLP

(57) ABSTRACT

A method of manufacturing a coated needle electrode comprising the steps 5 of holding an uncoated sharpened needle by the tip, dipping the uncoated sharpened needle into a bath of coating material, and withdrawing the sharpened needle from the bath of coating material. In this way, the coating can be applied after the needle has been sharpened thereby allowing more precision during the sharpening process. The invention also provides an apparatus for use with the method.

2 Claims, 6 Drawing Sheets

METHOD OF MANUFACTURING COATED NEEDLE ELECTRODES

CROSS REFERENCE TO RELATED APPLICATIONS

This application is a national phase application based on PCT/EP2008/055085, filed Apr. 25, 2008, which claims the priority of Danish Patent Application No. PA200700632, filed Apr. 27, 2007, and claims the benefit of U.S. Provisional Application No. 60/924,054, filed Apr. 27, 2007, the contents of all of which are incorporated herein by reference.

The current invention relates to a method of manufacturing coated needle electrodes. Coated needle electrodes are typically used for sensing electrical potentials in living tissue or for conducting electrical energy to such tissue. Needle electrodes are used in many different forms of therapy and/or diagnostic procedures. Two non limiting examples are tissue ablation and electromyography.

Coated needle electrodes generally comprise an elongated electrically conductive metallic shank which is sharpened at one end by grinding. Needle electrodes typically also have connection means attached to the other end for connecting said needle electrode to external electronic equipment. The metallic shank of the electrode is normally covered by an electrically insulating material so that only a small metallic area near the sharp tip will be in electrical contact with the tissue, hence the name "coated needle electrode".

DESCRIPTION OF RELATED ART

Needle electrodes are commonly manufactured by first cutting a metallic wire or tube to a desired length. The needle shank is then held fast near one end while the entire free shank is coated with an insulating material by spraying or dipping followed by curing and/or sintering of the coating. After the needle shank is coated, the coated tip is ground sharp whereby the insulating material is simultaneously removed from the electrode tip. Finally the connection means is electrically attached to the uncoated blunt end of the needle shank.

There are several drawbacks to this commonly used method of manufacturing needle electrodes:
1) The precision of grinding the sharp tip of the needle is affected by the concentric accuracy of the coating on the shank.
2) The coating may be damaged by the jaws which hold the shank still during grinding.
3) The transition from the coated shank of the needle to the conductive sharpened tip is effected by the concentric accuracy of the grinding, causing variations of the conductive surface area around the periphery of the tip.
4) Providing the needle with bevelled surfaces to form the sharp tip is not appropriate, since the conductive surface area will vary considerably around the periphery of the tip.

SUMMARY OF THE INVENTION

A first aspect of the current invention is therefore to provide an improved method of manufacturing coated needle electrodes, which provides improved precision when grinding the sharp tip of the needle electrode.

A second aspect of the current invention is to provide an improved method of manufacturing coated needle electrodes whereby the accuracy of the border line between the insulated portion and the non-insulated portion near the conductive tip can be improved.

A third aspect of the current invention is to provide an improved method of manufacturing coated needle electrodes which will also allow needle electrodes to be manufactured with multiple ring shaped conductive areas along the shank of the needle electrode at high precision and at low cost.

The above mentioned aspects are solved in part by providing a method as mentioned in the introductory paragraph comprising the steps of holding an uncoated sharpened needle by the tip, dipping the uncoated sharpened needle into a bath of coating material, and withdrawing the sharpened needle from the bath of coating material. In this way, it is possible to coat a needle after it has been sharpened. It is therefore possible to increase the precision of the sharpening. Furthermore, since the coating is applied to the needle after the sharpening process, the sharpening process does not damage the coating. The sharpening process can therefore use more effective clamping techniques. The method also allows different types of sharpening to be used, for example bevel sharpening of the tip, as in injection needles, can also be used.

In one embodiment of the method, the step of withdrawing the sharpened needle from the bath of coating material can be controlled such that the coating thickness is determined by the speed of the withdrawal. In this way, the coating can be very easily regulated.

In another embodiment of the method, the step of holding an uncoated sharpened needle by the tip could be provided by magnets.

The method could be applied with an apparatus which comprises a container of coating fluid into which the uncoated sharpened needle is dipped. In a preferred embodiment of the apparatus, the apparatus could comprise a suspension head which moves up and down in a vertical direction with respect to the bath of coating fluid and which comprises means for holding the needle suspended with its sharpened end upwards. By controlling the motion of the suspension head with respect to the level of the bath of coating fluid, the coating on the needle can be precisely controlled. In particular, the distance from the tip of the needle to the coating on the needle can be precisely controlled.

In one embodiment, the apparatus could further comprise a guide plate for guiding the needle. The guide plate could furthermore be arranged underneath the surface of the coating fluid in the container of coating fluid. In this way, the guide plate does not damage the coating on the needle during the withdrawal of the needle from the bath.

The apparatus could also comprise means for measuring the distance between the means for holding the needle and the surface of the bath of coating fluid. In this way, it is easy to control the coating, even if the level of the fluid changes over time.

In another embodiment, the suspension head could comprise a suspension guide element which supports the needle during the operation. This allows the needle to be supported, before the needle is inserted into the fluid bath.

The suspension head could also be made detachable from the rest of the apparatus. In this way, a number of suspension heads could be used to optimize the speed of the process. For example, one suspension head could be mounted in the machine and be involved in a dipping process, another suspension head could be getting loaded with needles, while a third suspension head could be placed in an oven for curing/sintering the coating fluid on the needles. Any number of suspension heads could be used together.

It should be emphasized that the term "comprises/comprising" when used in this specification is taken to specify the presence of stated features, integers, steps or components but does not preclude the presence or addition of one or more other features, integers, steps, components or groups thereof. For example, claim 1 uses the phrase "an electrode needle". However, the claim should be understood to comprise one, two, three, or any other number of electrode needles.

BRIEF DESCRIPTION OF THE DRAWINGS

In the following, the invention will be described in greater detail with reference to embodiments shown by the enclosed figures. It should be emphasized that the embodiments shown are used for example purposes only and should not be used to limit the scope of the invention.

DETAILED DESCRIPTION OF THE EMBODIMENTS

Figure 1:
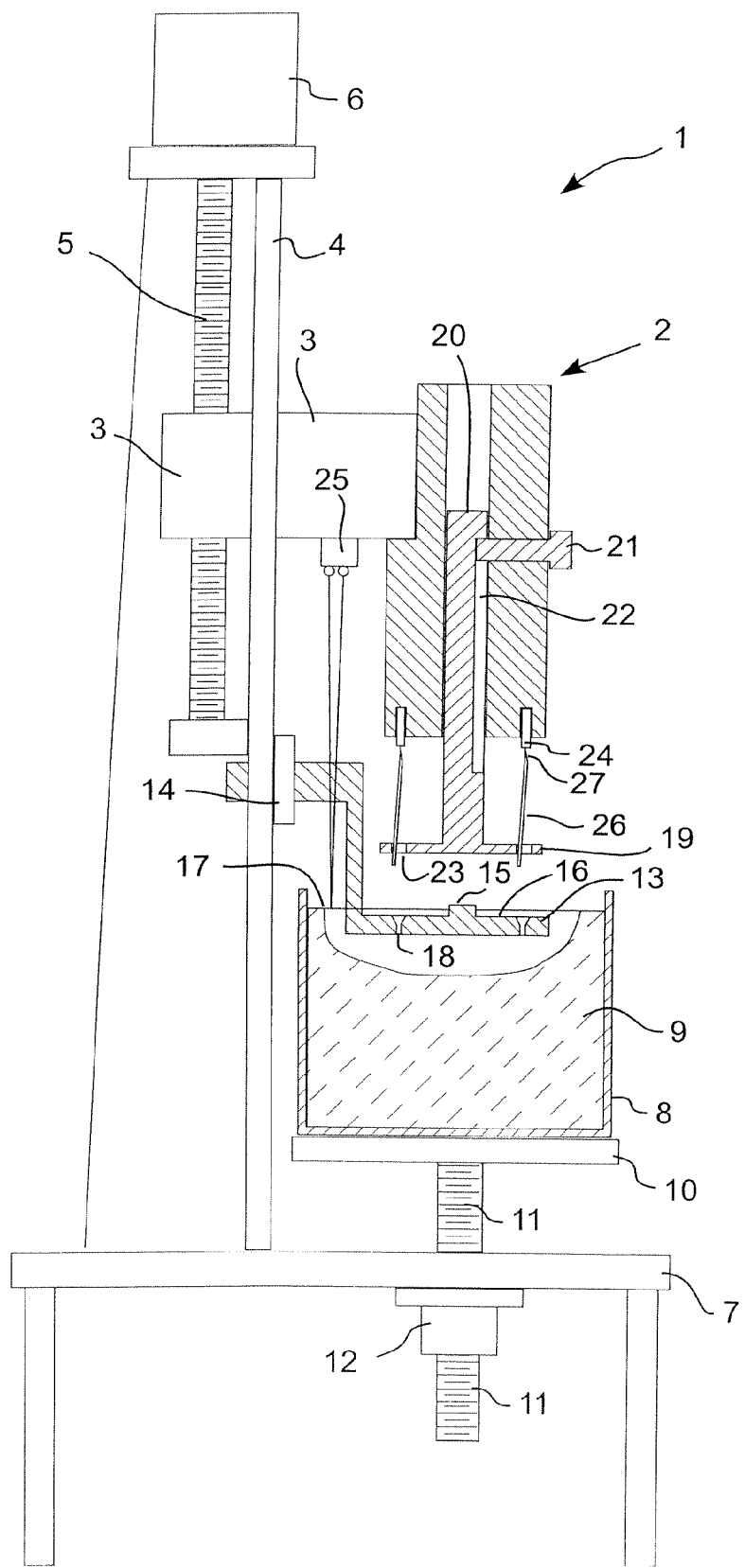
FIG. 1 illustrates a schematic representation of an apparatus for performing the coating step of the manufacturing method.

FIG. 1 shows one embodiment of an apparatus used in a method for manufacturing coated needle electrodes according to the invention. It is to be noted that the figures show the embodiments schematically and many of the details are not shown. The person skilled in the art should easily be able to fill in the missing details.

In the apparatus 1, a suspension head 2 is detachably fixed to a slide saddle member 3 which is slideably mounted on vertical guides 4 allowing the slide saddle member to linearly move up and down. The movement of the slide saddle member 3 is controlled by a linear drive screw 5. A servo motor drive 6 controls the direction and the speed of the movement. The frame of the vertical guides 4 is mounted on a horizontal frame member 7.

A container 8 filled with coating fluid 9 is supported by a plate 10 which is connected to the horizontal frame member 7 by means of a threaded shaft 11 and a threaded bushing 12. Via the threaded shaft and threaded bushing the vertical position of the container 8 can be adjusted. This can be used to compensate for changes in the fluid level in the container.

A needle guide plate 13 is submerged in the coating fluid 9. The needle guide plate is attached to the vertical guides 4 via an adjustment plate 14 which can be moved up and down if desired. It could also be fixed if desired. The needle guide plate 13 has stops 15 which protrude from the top surface 16 of the needle guide plate 13. In use the needle guide plate 13 is positioned such that the top surface 16 of the needle guide plate is positioned just under the surface 17 of the coating fluid 9 and the top surface of the stops 15 is just above the surface 17 of the coating fluid 9. In the current embodiment, the needle guide plate is circular in shape and comprises a circular array of through going holes 18 which are tapered at their upper side.

A needle suspension guide plate 19 is slideably connected to the suspension head 2 by means of guiding shaft 20. The shaft 20 is restricted to purely axial movements by a pin 21 which slides in a groove 22 so that the needle suspension guide plate 19 cannot rotate. The pin 21 is fastened to the suspension head. As with the needle guide plate 13, the needle suspension guide plate 19 is circular in shape and comprises a circular array of through going holes 23 or guide holes.

A circular array of magnets 24 is embedded in the suspension head 2. Due to the arrangement of the apparatus, the magnets are kept aligned with the through going holes in the needle suspension guide plate 19 and the through going holes 18 in the needle guide plate 13.

A laser based distance measuring module 25 is attached to the saddle member 3 for continuously measuring the distance from the saddle member 3 to the surface of the coating fluid 9 during the motion of the suspension member 2. Since the distance between the lower surface of the magnets and the saddle member is constant, the laser beam distance measuring module can precisely measure the distance between the bottom surface of the magnets 24 and the surface 17 of the coating fluid 9. The laser measuring module is electrically connected to a control module which can calculate the distance.

In use needles to be coated 26 are hung from the magnets by their sharpened ends. Since the tips of the needles are in contact with the bottom surface of the magnets, and since the controller, via the laser based distance measuring module 25 knows the precise location of the bottom surface of the magnets with respect to the coating fluid, the controller also knows the precise distance from the tip of the needle to the surface of the coating fluid.

Figures 2, 3, 4:
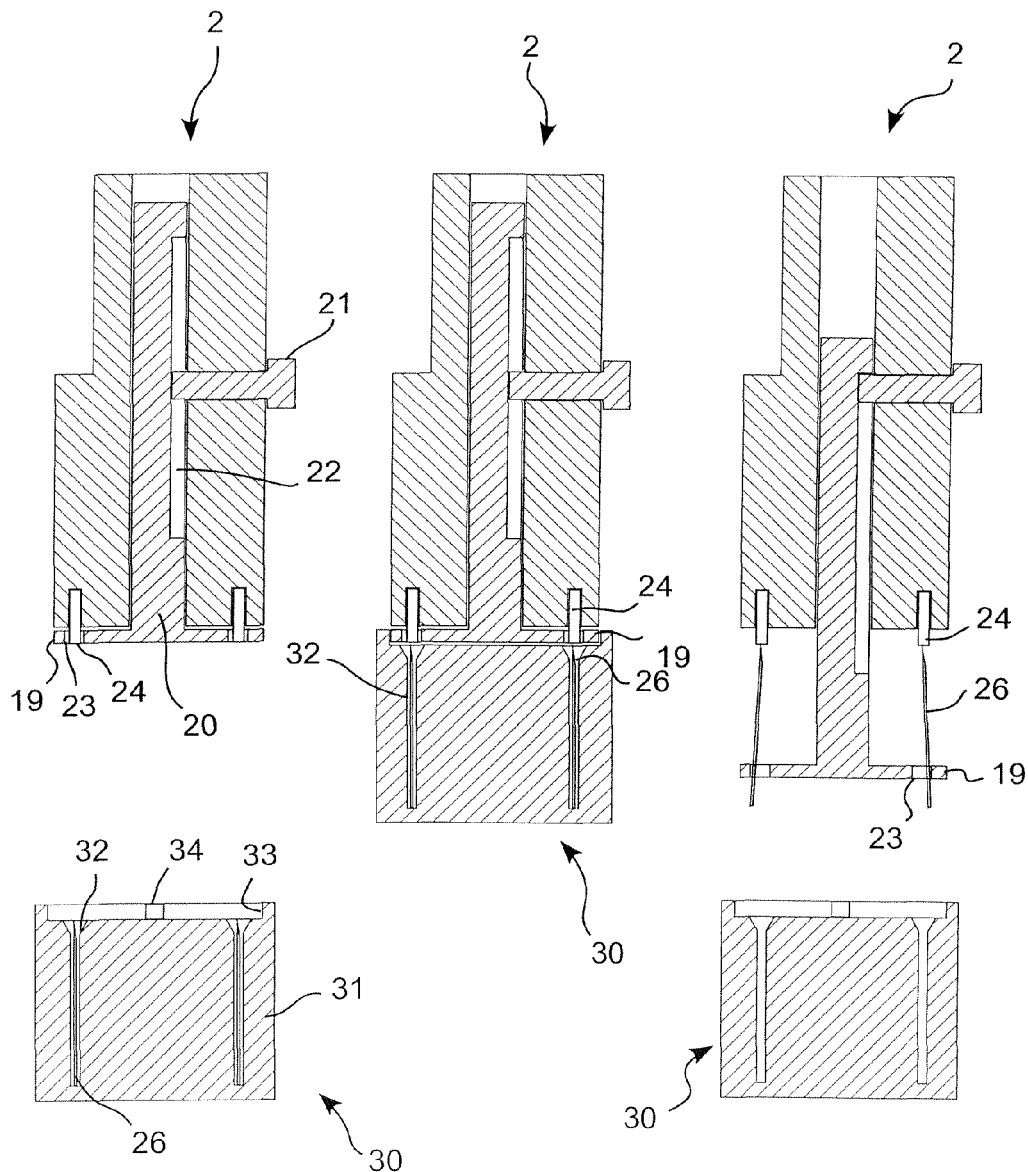
FIGS. 2-4 show schematic sectional views of a suspension head and a loading fixture at three different points of the loading process.

FIG. 2 shows the suspension member 2 when it has been removed from the apparatus and a sectional view of a loading fixture 30 for loading the needles 27. As can be seen from FIG. 2, the suspension needle guide plate 19 has been moved into its uppermost position. In this position, the magnets embedded in the suspension head are arranged to extend out through the through going holes 23 in the suspension needle guide plate 19. In this embodiment, the depth of the suspension needle guide plate has substantially the same depth as the free end of the magnets.

The loading fixture 30 comprises a circular body 31 made from a non-magnetic material. The circular body has an array of elongated recesses 32. The depth of the elongated recesses is approximately equal to the length of the needles 27 which are to be coated. The recesses are tapered at the open end for easy insertion of the needles. A guide surface 33 and an index key 34 are dimensioned to fit around the suspension needle guide plate 19 of the suspension assembly.

The loading fixture allows the needles to be easily inserted into the loading fixture with the sharpened ends at the top. Once all the needles have been loaded into the loading fixture, the loading fixture is moved into a position where it engages the suspension needle guide plate of the suspension head. This is shown in FIG. 3. In this position, the magnets are aligned with the needles and the sharpened tips of the needles therefore clip onto the magnets.

Once the magnets have engaged with the needles, the loading fixture can be withdrawn from the suspension head. At the same time as the loading fixture is withdrawn, the suspension needle guide plate 19 is also moved down. This has the effect that the needles are kept substantially aligned with the longitudinal axis of the suspension head. The guide plate 19 thereby prevents the needles from swinging around and either falling off the magnets or clipping on to each other due to the magnetic forces present in the system. When the movement of the guide plate shaft 19 is stopped by the pin 21 and the loading fixture 30 is removed, the needles 26 will stay suspended from the magnets via the tips of the needles and be supported near their unsharpened end against the walls of the through going holes 23 of the suspension needle guide plate 19. This is shown in FIG. 4.

Figure 5:
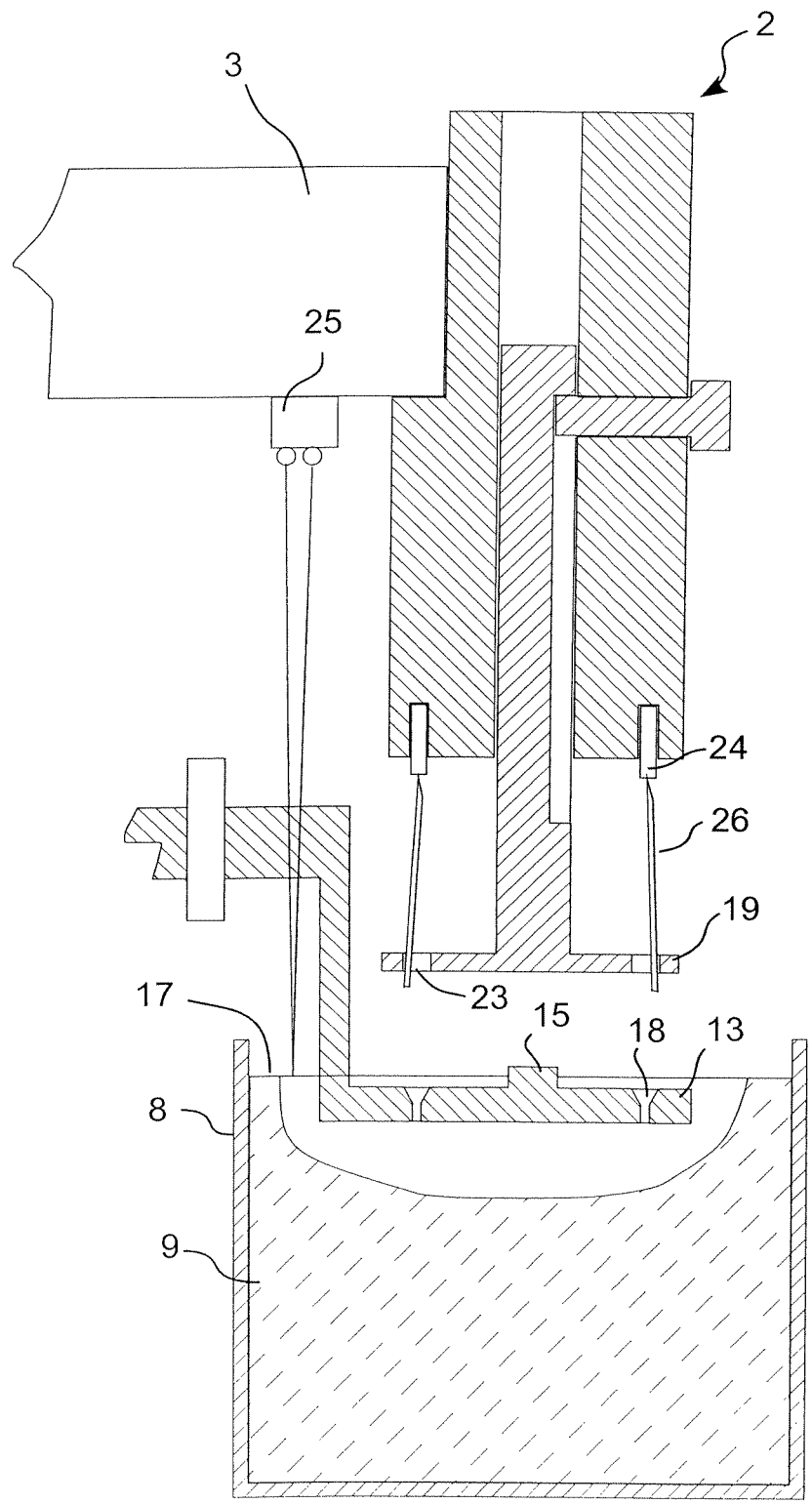
FIG. 5 is a schematic sectional view showing the needles suspended in the dip coating apparatus prior to being coated.

FIG. 5 shows the suspension head with the needles suspended as described above, but after the suspension head has been reconnected to the dip coating apparatus 1.

Figure 6:
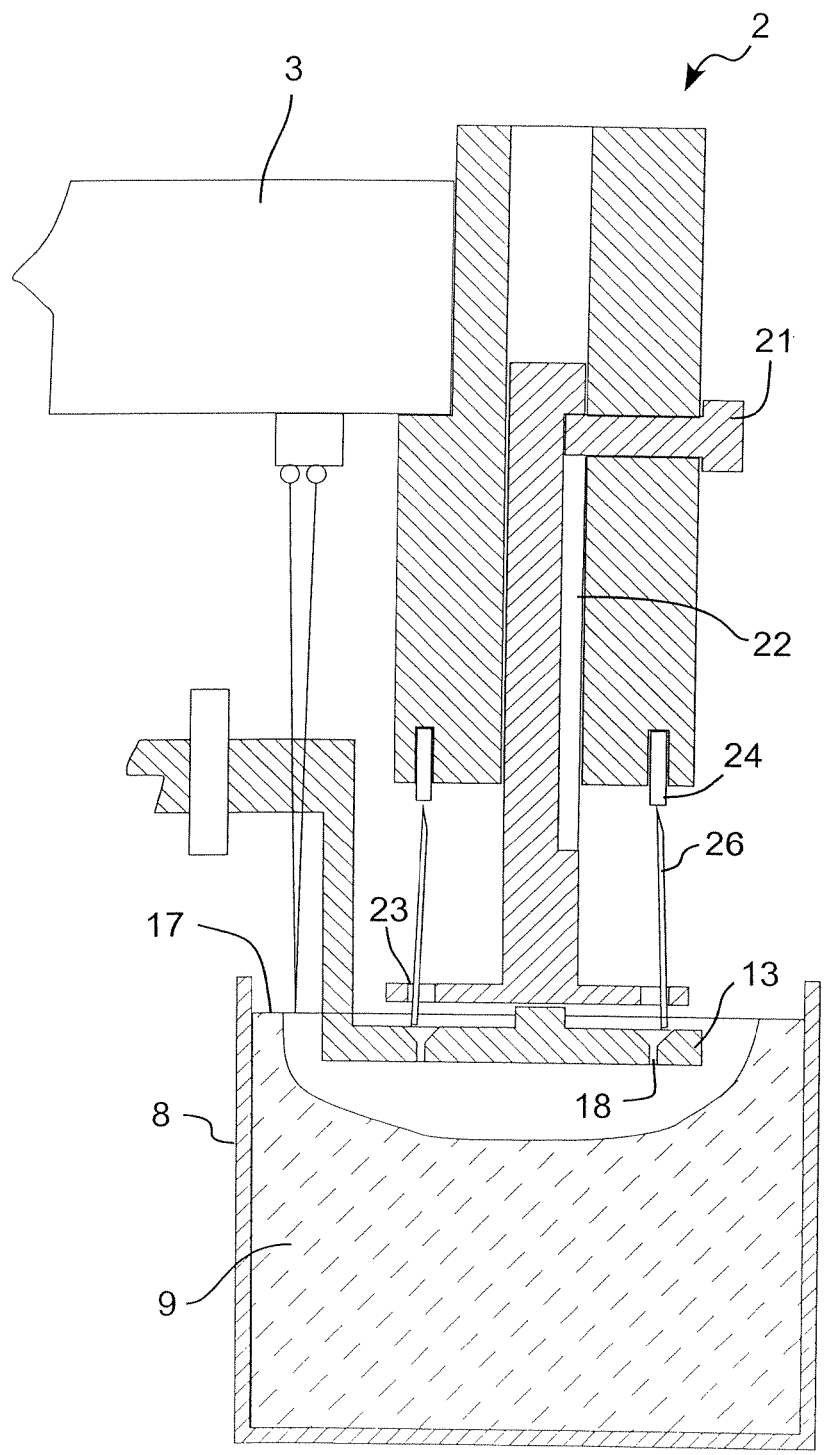
FIG. 6 is a schematic sectional view of needles suspended in the dip coating apparatus just before the needles enter the bath of coating fluid.

FIG. 6, shows the suspension head where it has been moved down into a position where the needles have just entered below the fluid surface and have engaged the tapered ends of the through going holes 18 in the needle guide plate 13 which is immersed in the fluid. It is to be noted that in the position shown in FIG. 6, the suspension needle guide plate 19 is in contact with the upper surface of the stops 15 on the needle guide plate 13. Since the upper surface of the stops 15 is arranged above the surface of the coating fluid 9, the suspension needle guide plate 19 is prevented from coming into contact with the coating fluid.

As the movement of the suspension head 2 continues downwardly, the lower end of the needles will slide down through the narrow end of the guide holes 18 in the needle guide plate 13, whereby the needle shanks are forced away from the walls of through going holes 23 in the suspension needle guide plate 19 as shown in FIG. 6.

Figure 7:
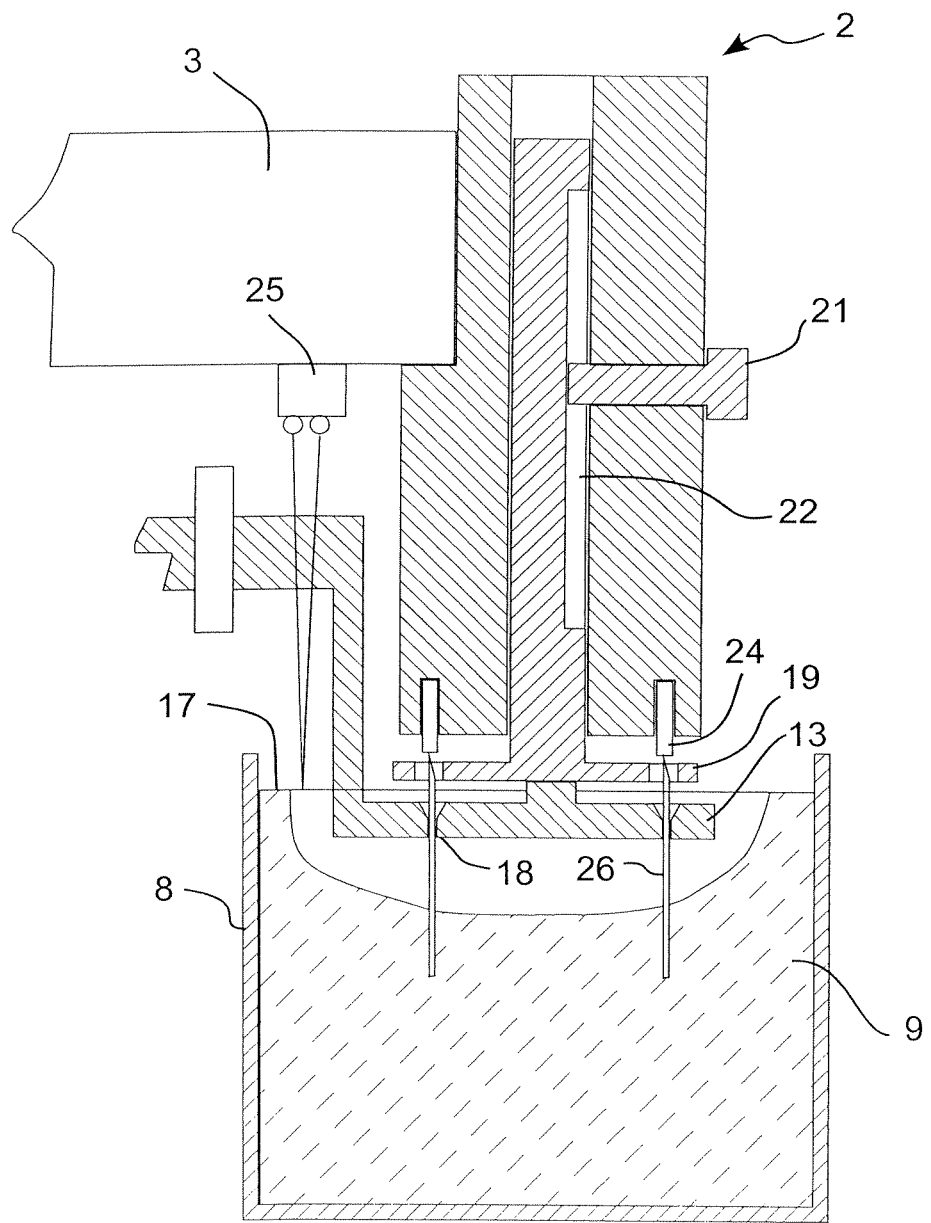
FIG. 7 is a schematic sectional view of the needles suspended in the dip coating apparatus at the time just before the needles are withdrawn from the bath of coating fluid.

In the position shown in FIG. 7, the needle shanks 26 are now submersed in the coating fluid to a precise depth as determined by the distance from the lower surface of the magnets to the fluid surface. This distance is continuously measured by the laser distance measuring unit 25. The control unit can therefore control the servo unit such that this distance is precisely controlled, even if the depth of the fluid should change over time.

Since the guide holes 23 in the suspension needle guide plate 19 allow the free ends of the magnets to pass through, the depth of the immersion may include the full length of the shank of the needle all the way up to the sharpened tip. Furthermore, any other precise location on the shank may also be selected if desired. When the selected depth of immersion is reached, the control unit will reverse the servo motor drive 24 and withdraw the needles at a predetermined speed. The speed of withdrawing the needles from the surface of the fluid, together with the coating characteristics of the fluid determine the coating thickness.

It should be noted that the needles are only in contact with the guide holes 18 in the needle guide plate 13 below the fluid surface. The guide holes will therefore not affect the integrity of the coated layer on the needles while they are being withdrawn from the fluid. Furthermore, since the guide holes in the needle guide plate 13 prevent the needle shank from contacting the guide holes 23 in the suspension needle guide plate 19, the coated surface will not be damaged by the guide holes 23 in the suspension needle guide plate 19 until the end of the needles are released by the guide holes 18 in the needle guide plate 13. Once the needles are released by the guide holes in the needle guide plate 13, the end of the needle shank will again contact the walls of the guide holes 23 in the suspension needle guide plate 19. However, the damage caused to the coated surface by this contact will be in the area at the end of the needle shank, which is also the area where the electrical connection is performed. It is therefore necessary to remove the coating in this area anyway, whereby the damage is of no consequence.

At the end of the coating procedure, the suspension head assembly 2 with the coated needles is detached from the saddle member 3 and transferred to an oven for curing or sintering of the coating.

When the coating has cured, electrical connection means (not shown) for connection to external electronic apparatus is attached to the blunt end of the needles.

In another embodiment of a method according to the invention, a needle electrode is provided which comprises multiple layers of electrically insulating material and electrically conductive material. In this way, it is possible to create needle electrodes having more than one conductive electrode surface along the shaft of the needle. The method includes the following steps:

1. Coating the sharpened needle shank with an electrically insulating material to a precise first distance from the sharp tip by help of the described coating method.
2. Coating the needle shank on top of the first insulating coating with an electrically conductive material to a precise second distance from the sharp tip by help of the described coating method, said second distance being greater than said first distance.
3. Coating the needle shank on top of the conductive coating with an electrically insulating material to a precise third distance from the sharp tip by help of the described coating method, said third distance being greater than said first and second distance.
4. Exposing a surface of each layer of conductive coating near the blunt end of the shank.
5. Attaching electrical connection means to each of the exposed layers of conductive coating near the blunt end of the shank The method could be started by cutting a wire or tube into pieces having a precise length and then sharpening the tip of one end to form a needle.

The method could also repeat steps 2 and 3 until a desired number of conductive electrode ring surfaces isolated from each other have been created along the shaft of the needle.

The coating can be removed from the blunt end of the needle shank in order to connect connection means via different methods, two examples are grinding and scraping.

Figure 8:
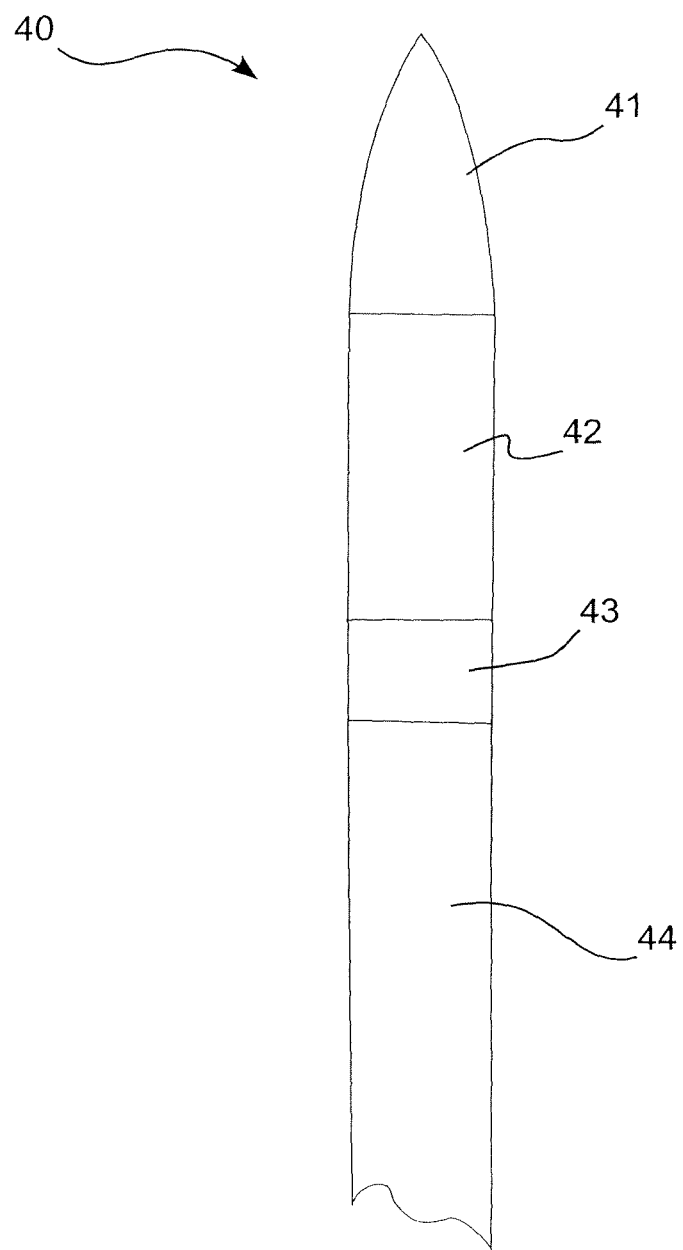
FIG. 8 schematically shows one embodiment of a needle electrode with multiple ring areas of insulated electrodes along the shank.

FIG. 8 shows a needle electrode 40 with two electrode surface areas 41, 43 along the shaft. The first electrode surface area 41 is the sharp metallic tip of the needle. The second electrode surface area 43 is a ring formed layer of conductive material. Between the first and second electrode surface areas is a ring formed portion 42 of a first layer of insulating material. Below the second electrode surface area 43 is a second layer 44 of insulating material.

The description presented above has described one embodiment of an apparatus which is suitable for performing the method according to the current invention. However, the person skilled in the art will understand that the method could be performed with other machines and/or apparatuses. The scope of the invention should therefore not just be limited to the embodiment shown in the figures and described in this description.

For example, the embodiment described above has shown a suspension head and guide plates which were circular in shape and having a circular array of magnets/guide holes. However, the shape of the suspension head and the shape of the array could take many different forms. For example, a rectangular suspension head and rectangular guide plates with a rectangular array of magnets/guide holes could be imagined.

Another example is that the current embodiment has used magnets in order to hold the needles connected to the suspension head. However, the person skilled in the art will realize that means other than the magnets could also be used for precise attachment of the sharp needle tips in the dipping apparatus without changing the scope of the invention. One example is a thin layer of adhesive gel material. Another example is a layer of self closing elastomeric material compounded for high friction properties. The magnetic forces holding the needles in the embodiment described will be replaced, in these two examples, by adhesive forces and friction forces respectively.

It should also be noted that many other steps can be added to the method. For example, depending on the use of the coating fluid, it could be useful to coat the needle electrode with a lubrication coating after the first coating process.

It is to be noted that the figures and the above description have shown the example embodiments in a simple and schematic manner. Internal electronic and mechanical details have not been shown since the person skilled in the art should be familiar with these details and they would just unnecessarily complicate this description. For example, the control system has not been described in great detail, since a person skilled in the art of control systems would be able to design a control system based on this specification. Also, the mechanical details of the connections between the suspension head and the saddle, between the saddle and guide means, etc are all details which a person skilled in the art of designing mechanical systems would be able to provide.

The invention claimed is:

1. A method of manufacturing a coated needle electrode comprising the steps of:
    holding an uncoated sharpened needle by the tip by a magnet, where the contact between the magnet and the needle is limited to the end of the sharpened tip of the needle,
    dipping the uncoated sharpened needle into a bath of coating material, and
    withdrawing the sharpened needle from the bath of coating material.

2. Method according to claim 1, characterized in that the step of withdrawing the sharpened needle from the bath of coating material is controlled such that the coating thickness is determined by the speed of the withdrawal.

* * * * *